US011579136B2

United States Patent
Silva et al.

(10) Patent No.: US 11,579,136 B2
(45) Date of Patent: Feb. 14, 2023

(54) DATING PETROLEUM RESERVOIR FLUID RESIDENCE TIMES

(71) Applicant: UTI Limited Partnership, Calgary (CA)

(72) Inventors: Renzo Correa Silva, Calgary (CA); Lloyd Ross Snowdon, Calgary (CA); Haiping Huang, Calgary (CA); Stephen Richard Larter, Calgary (CA)

(73) Assignee: UTI Limited Partnership, Calgary (CA)

( * ) Notice: Subject to any disclaimer, the term of this patent is extended or adjusted under 35 U.S.C. 154(b) by 119 days.

(21) Appl. No.: 16/802,506

(22) Filed: Feb. 26, 2020

(65) Prior Publication Data
US 2020/0278336 A1    Sep. 3, 2020

Related U.S. Application Data

(60) Provisional application No. 62/812,840, filed on Mar. 1, 2019.

(51) Int. Cl.
G01N 33/28    (2006.01)
(52) U.S. Cl.
CPC .................. *G01N 33/2823* (2013.01)
(58) Field of Classification Search
CPC .............................................. G01N 33/2823
See application file for complete search history.

(56) References Cited

PUBLICATIONS

Bailey D., van Aswegen A., Todd-Pokropek A. and Humm J. eds. (2015) Nuclear Medicine Physics: A Handbook for Teachers and Students. 1st ed., International Atomic Energy Agency.
Bücker C. and Rybach L. (1996) A simple method to determine heat production from gamma-ray logs. Mar. Pet. Geol. 13, 373-375.
Curiale J. A. and Frolov E. B. (1998) Occurence and origin of olefins in crude oils. A critical review. Org. Geochem. 29, 397-408.
Frolov E. B. and Smirnov M. B. (1994) Unsaturated hydrocarbons in crude oils. Org. Geochem. 21, 189-208.
Frolov E. B., Melikhov V. A. and Smirnov M. B. (1996) Radiolytic nature of n-alkene/n-alkane distributions in Russian Precambrian and Palaeozoic oils. Org. Geochem. 24, 1061-1064.
Frolov E. B., Melikhov V. A. and Vanyukova N. A. (1998) Olefins of radiogenic origin in crude oils. Org. Geochem. 29, 409-420.
Larter et al, The dating of fluid residence time in subsurface reservoirs. Challenges, strategies and a design schematic for a practical geochemical toolbox, CSPG Gussow 2017.
Larter S., Oldenburg T., Marcano N., Snowdon L., Adams J. and Chanthramonti K. (2012) New routes to solutions of the WCSB oil charge conundrum: γ-ray Photons and Fourier Transform Mass Spectrometry. In GeoConvention 2012: Vision Calgary. pp. 1-6.
Larter et al. The dating of petroleum fluid residence time in subsurface reservoirs. Part 1: A radiolysis-based geochemical toolbox Geochimica et Cosmochimica Acta 261 (2019) 305-326.

(Continued)

*Primary Examiner* — Mark R Gaworecki
(74) *Attorney, Agent, or Firm* — FisherBroyles, LLP; Anthony J. DoVale

(57) ABSTRACT

Methods are provided for determining the residence age of petroleum fluids in subsurface reservoirs. The methods facilitate the determination of the geological timing of the emplacement of a petroleum fluid in a porous reservoir, as distinct from the timing of petroleum generation in, and expulsion from, a source rock.

20 Claims, 6 Drawing Sheets

(56) References Cited

PUBLICATIONS

Marcano et al The dating of fluid residence time in Petroleum and CO2 storage reservoirs. Part 1: Challenges and a design schematic for a practical geochemical toolbox, IMOG, 2015.
Blum, Peter. PP Handbook Nov. 1997. Natural gamma radiation. Chapter 5.
Silva et al, Routes and progress in age dating fluid residence time in subsurface reservoirs: Issues and E&P Applications. Geoconvention, Calgary, Canada May 7-11, 2018.

DATING PETROLEUM RESERVOIR FLUID RESIDENCE TIMES

FIELD

Techniques are disclosed for determining the residence age of petroleum fluids in subsurface reservoirs, involving assays that quantify selected radiolysis decomposition products.

BACKGROUND

In petroleum systems, much effort has been put into using forward basin models to estimate the times of petroleum charging into subsurface traps. There are however no independent constraints on these estimates, yet fluid residence age in a petroleum trap is a key factor in many aspects of petroleum systems evaluation. While oilfield locations and oil maturity are often used together with basin models to constrain those models, the direct testing of the locations of accumulations is provided by drilling, and estimates of the times of charging from models are non-unique and unreliable. While forward basin models provide estimates of petroleum generation timing using various kinetic models, the timing of expulsion from the source rock and the often poorly defined duration of secondary and tertiary migration to and from the reservoir, are unconstrained by real measurements made on the crude oil and may have large errors associated with them, extending to a significant portion of the age of a reservoir.

Petroleum charge times and rates are key variables in controlling hydrocarbon prospectivity, as they define volumes of trapped petroleum and the dynamics of trap integrity, including leakage and alteration phenomena. Knowledge of the timing of reservoir trap and seal development relative to the migration of crude oil accordingly reduces exploration risk.

Nuclear radiation in rocks is primarily generated from the alpha-emitting decay of uranium ($^{238}$U) and thorium ($^{232}$Th) isotopes, and also from the beta particle emitting decay of potassium ($^{40}$K). The primary particles emitted from decaying radionuclides, however, are rapidly stopped by interactions with atoms in the host minerals and are mostly attenuated within the grains of the host minerals themselves, ultimately releasing, through a complex chain of interactions and daughter species, energized electrons and photon radiation in the form of gamma rays. Some neutrinos are also released but these do not interact significantly with reservoir media.

The main form of nuclear radiation that interacts with reservoir fluid media are primary gamma ray photons and subsequently scattered, lower energy gamma ray and x-ray photons. The interaction of gamma ray photons with atoms in fluids (or other phases) has a few possible outcomes. The photon can disappear and be absorbed completely through the photoelectric effect emitting a photoelectron, pair production, nuclear triplet production or a photonuclear reaction. Also, a gamma ray photon can be scattered and change its direction but keep its energy (Rayleigh scattering) or lose part of its energy through the Compton effect, whereby photons interact with electrons in atoms, losing energy and producing lower energy photons as a result (Bailey et al. 2015). Compton effect scattered gamma ray photons ultimately become X-rays and then finally infrared photons, and thus the energy of radionuclide fission ends up as thermal energy in the rock. Compton scattering is the primary radiation attenuation mechanism for gamma ray photons of up to a few million electron volts energy that interact with atoms typical of the major rock forming elements, such as silicon, oxygen, aluminium, calcium, magnesium, sodium, iron etc. Compton scattering also ultimately produces an avalanche of low energy electrons (10 to 80 electron volts), into the irradiated medium. Interactions of petroleum fluid with this avalanche of low energy electrons are the primary cause of the observed radiolysis chemistry effects on organic materials such as petroleum.

Crude oils are very reactive under high radiation doses, with excited hydrocarbon and heteroatomic molecules being created through non-selective bond breaking and bimolecular recombination reactions including hydrogen loss, condensation processes and reactions between any species present, including water, $N_2$ and $CO_2$, also occurring. Classical geochemical proxy routes to assess petroleum system variables commonly involve one or a few related precursors, converting reversibly or irreversibly, to one or a few closely related products. Specific radiolysis products are often hard to measure, as large numbers of low concentration species are produced from even simple binary compound mixtures (Larter et al., 2012).

Frolov et al. (1998) and Curiale and Frolov (1998), described the production of alkenes in crude oils from natural radiation damage (radiolysis), with radiation dose-related impacts. In petroleum mixtures, radiation-induced unsaturation has a very complex distribution with double bonds appearing through essentially all organic fractions, making detection of radiation-induced daughter species by classical geochemical approaches, such as gas chromatography-mass spectrometry (GC-MS), very challenging. Therefore, a bulk technique for measuring double bond production, such as is available using spectroscopic approaches, such as nuclear magnetic resonance (NMR), are better suited to accurately assess alkene production (Frolov and Smirnov, 1994; Frolov et al., 1996; Frolov et al., 1998).

SUMMARY

Methods are provided for determining the residence age of petroleum fluids in subsurface reservoirs. In particular, the impact of radiation from radioactive decay of radiogenic nuclides in a reservoir rock on trapped petroleum fluid composition is demonstrated herein to provide a viable route to an age dating proxy. In such methods, a sample, or series of samples, from the reservoired fluid is obtained, for example by way of typical oilfield approaches to drilling and sampling. A set of laboratory irradiation experiments are used to determine: the matrix-specific sensitivity of the individual petroleum samples to radiolysis-induced alterations; and, the attenuation coefficients for gamma radiation of sampled reservoir solid matrix materials. A plurality of analyses may then be used to determine the concentration of radiolysis proxies in the original samples and the irradiated analogs. Reservoir and fluid properties are used to determine the radiation dose absorption rate of reservoired fluids. Mixing processes within the reservoir may be assessed, for example using a mass transport model, coupling petroleum irradiation, petroleum radiolysis processes, transport of age dating proxies through fluid advection and diffusion. The residence age may be determined using both the sample accumulated radiation dose determined chemically using the petroleum samples and assessed radiation dose rates from the reservoir measured using geophysical logs or chemical analysis of radioactive elements.

In various aspects, the present method reflects the recognition that locally varying reservoir gamma ray dose, relating to local radionuclide distribution in the reservoir, will be a definitive local source signal, measured using a gamma ray log or other method, for any reservoir fluid based radiation impacts, as gamma ray penetration distances are on the order of a meter, and thus detection of locally generated radiolysis effect profiles, on top of any background level of proxy inherited from the primary oil charge, is a route to decoupling source rock versus reservoir rock incurred radiation impacts. This, in turn, requires that compositional profiles through an oil column must be made, to provide an effective chronometer, that may for example accommodate mass transport effects and fluid mixing processes. Compositional profiles obtained by analysis of the reservoir and petroleum may be incorporated into mixing models as an element in such data analysis, for example to define the proximity of reservoir locations that may be assumed to contain fluids of the same age. The variability of gamma ray penetration as function of physical and chemical properties of both the source and reservoir rock may be included in the calibration parameters of the system model. If calibrated for the reservoir radioactive isotope load, measurement of radiation dose profiles in reservoired petroleum, assessed by chemical or isotopic analysis of crude oil species or gases (e.g. $CH_4$, $CO_2$ or $C_2H_4$), can provide routes to dating reservoir fluid residence age. The present methods may accordingly involve sampling, chemical analysis of both petroleum and reservoir material, data analysis, and may further make use of models that couple petroleum charging, reservoir radiolysis and mass transport processes related to advection and diffusion.

Aspects of the present methods involve dating the residence age of a hydrocarbon reservoir fluid in a hydrocarbon reservoir, by:

determining local matrix radiation dose rates for a solid reservoir matrix at a plurality of locations, and selecting a plurality of distinct sample locations within the reservoir each having a distinct matrix radiation dose rate of a matrix radiation;

obtaining a plurality of reservoir fluid samples from two or more of the distinct sample locations, wherein the reservoir fluid in the samples comprises a radiological proxy moiety that is a marker for a proxy chemical transformation of the reservoir fluid in response to a total radiation dose of the matrix radiation over a geological time span, for example being more than 1, 2, 3, 4, 5, 10 or 20 million years, and wherein a proxy chemical transformation rate in response to an metered radiation dose of the matrix radiation is such that a changing concentration of the radiological proxy is measurable over a measurement time span that is less than 1 year, where the metered radiation dose rate is greater than the natural matrix radiation dose rates, for example being less than 5, 10, 15, 20 or 25 times the greatest of the matrix radiation dose rates;

determining the concentration of the radiological proxy in the reservoir fluid samples from distinct sample locations, the concentration of the radiological proxy in each sample being proportionate to a total radiation dose for the reservoir fluid sampled at each of the respective sample locations, so that a total radiation dose signal for each sample (Q_total) can be calculated from the concentration of the radiological proxy in each sample;

calculating the nominal duration of exposure of each of the reservoir fluid samples to the respective matrix radiation dose rates based on the calculated total radiation dose signal for each sample;

setting a concentration of source rock derived radiation dose proxy in the reservoir fluid at a constant value (Q_source) for at least two of the sample locations, being proximate sample locations within 10 meters of each other in the reservoir, then subtracting Q_source from Q_total for each sample to obtain a local in-reservoir radiation dose signal (Q_reservoir) for each sample; and, assuming the same residence age (RA) for fluids within a reservoir zone containing the proximate sample locations, determining an emplacement time, at which the reservoir fluid samples from the proximate sample locations each became subject to the distinct matrix radiation dose rates at each respective proximate sample location, the difference between present time and the emplacement time being the RA of the hydrocarbon reservoir fluid in the reservoir zone containing the proximate sample locations.

These methods may also involve determining the RA of the hydrocarbon reservoir fluid at a plurality of reservoir zones, each respectively containing at least two proximate sample locations. The matrix radiation may for example be gamma radiation. The radiological proxy moiety may for example be a measured concentration of olefin hydrogens. The metered radiation may include gamma ray photons with an energy between 0.5 and 2.5 MeV, at dose rates ranging from 0.01 Gy/h to 20 or 30 Gy/h.

Methods may involve measuring a concentration of the radiological proxy in a source rock for the hydrocarbon reservoir. Methods may also involve determining a rate of chemical transformation of the radiological proxy compound in response to the metered radiation dose over a measurement time span that is less than 1 month or 1 year.

Methods for dating the residence age (RA), of a petroleum fluid in a petroleum reservoir may accordingly involve:

determining the local matrix nuclear radiation dose rates for a solid reservoir matrix at one or more locations ($dr_Q$), and selecting one or more distinct sample locations within the reservoir each having a distinct matrix radiation dose rate of nuclear radiation;

obtaining reservoir petroleum fluid samples from one or more distinct sample locations, wherein the reservoir fluid in the samples contains a radiological proxy moiety that is a marker for a proxy chemical transformation of the reservoir fluid in response to a total radiation dose absorbed from matrix radiation over a geological time span, and where the proxy chemical transformation rate in response to a metered radiation dose of the matrix radiation can be determined in the laboratory by irradiation of fluid samples at dose rates higher than those found in a geological environment;

determining the concentration of the radiological proxy in the reservoir fluid samples from the distinct sample locations, the concentration of the radiological proxy in each sample being proportionate to a total radiation dose for the reservoir fluid sampled at each of the respective sample locations, so that a total radiation dose signal for each sample ($Q_{total}$) can be calculated from the concentration of the radiological proxy in each sample;

assessing the fractional contribution of the local reservoir radiation dose ($Q_{reservoir}$), to the total radiation dose received by the fluid sample during its complete history from the source rock through to the reservoir; and, calculating the nominal duration of exposure within the reservoir, of each of the reservoir fluid samples (RA), to the respective local reservoir radiation dose rates ($dr_Q$), based on the calculated local radiation dose signal for each sample obtained from the proxy concentration, and the local radiation dose rate.

DETAILED DESCRIPTION

Figure 1:
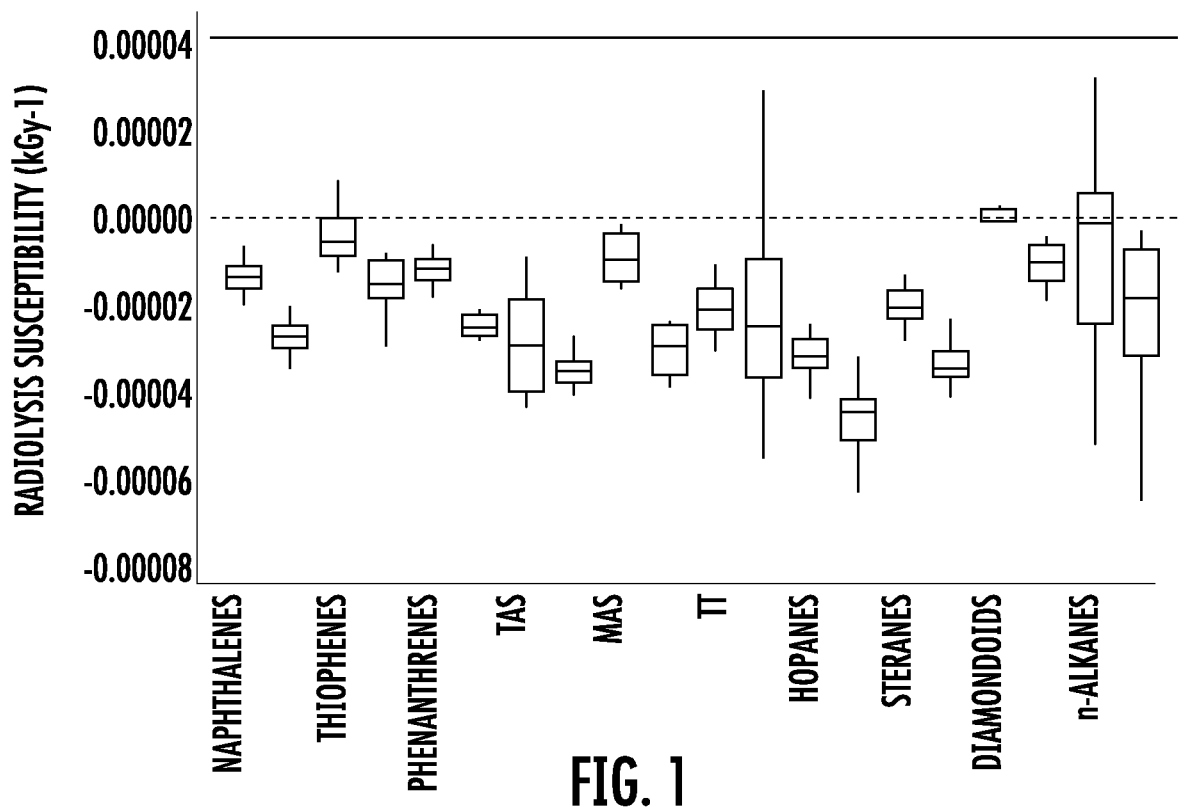
FIG. 1 is a box plot illustrating the distribution of radiolysis susceptibility of monitored compounds, as grouped by compound class, for AHO (red) and NSO (blue) irradiated crude oil sample sets. The gamma ray radiolysis susceptibility ($kGy^{-1}$) of the different compounds is derived by normalizing the gradient (slope), for each compound, in the linear trend of compound concentration versus radiation dose, to the compound original concentrations in the parent oil for each monitored chemical compound or class. TAS=triaromatic steroid hydrocarbons, MAS=monoaromatic steroid hydrocarbons, TT=tricyclic terpanes. On the box plot, maximum and minimum values for each compound class are represented by whiskers, while the top and bottom of the boxes represent first and third quartiles of the data.

In the context of the present application, various terms are used in accordance with what is understood to be the ordinary meaning of those terms. For example, as used herein, "petroleum fluids" includes any of the following: oil (often referred to as petroleum), shale oil (oil naturally produced from shale reservoirs), oil sands bitumen, natural gas, gas condensate, tar, bitumen, and other known hydrocarbons. In this context, "petroleum" is a naturally occurring mixture consisting predominantly of hydrocarbons in the gaseous, liquid or solid phase. In the context of the present application, the words "petroleum" and "hydrocarbon" are used to refer to mixtures of widely varying composition. In particular, petroleum in a reservoir is not limited to hydrocarbons, and may include, for example, trace quantities of metals (e.g. Fe, Ni, Cu, V, Co etc), in addition to numerous compounds containing N, S, O, in addition to carbon and hydrogen. "Fluids", such as petroleum fluids, include both liquids and gases. Natural gas is the portion of petroleum that exists either in the gaseous phase or in solution in crude oil in natural underground reservoirs, and which is gaseous at atmospheric conditions of pressure and temperature. Natural gas may include amounts of non-hydrocarbons. In this context, a "reservoir" is a subsurface formation containing one or more natural accumulations of moveable petroleum, which are generally confined by relatively impermeable rock. A "zone" is a section of a formation or reservoir, and as used herein is a relative term, meaning in general that the relevant zone is characterized by the recited features that describe the zone.

As used herein, "radiolysis" refers to the processes that cause compositional alterations to organic matter when submitted to ionizing irradiation, such as gamma rays, X-rays, high energy electrons, alpha or beta particles or other nuclear particles including protons or neutrons. A "natural radiation dose" refers to radiation absorbed by petroleum reservoir fluids during their geological timescale history. A "laboratory radiation dose" or "metered radiation dose" refers to radiation absorbed by samples in laboratory experiments whereby samples are exposed to known dose rates and total doses of nuclear radiation.

As used herein, "radiolysis proxies" refer to the abundances or ratios of molecular species or functional groups in a sampled petroleum fluid that can be related by theory or laboratory calibration to absorbed nuclear radiation dose. They are chemical compositional parameters that correlate with absorbed nuclear radiation dose.

As used herein, a fluid "residence age" refers to the time period that a given fluid, such as petroleum, resides in a specific part or zone of a formation or petroleum reservoir.

Component elements, steps and elemental technologies that make up aspects of the present methods include the following:
i. Sampling well test, production or reservoir core fluids and reservoir media to create a sample set for analysis.
ii. Identifying, selecting and measuring appropriate chemical radiolysis proxies, based on susceptibility of petroleum to radiolysis, concentration in the petroleum, resistance to other forms of in reservoir alteration processes and their ease of analytical detection and measurement.
iii. Assessing the total natural radiation doses ($Q_{total}$) experienced by petroleum fluids in natural reservoirs.
iv. Decoupling the radiolysis impacts on proxy concentrations in petroleum derived from radiolysis in the parent source rocks and carried over into the reservoir ($Q_{source}$) from the radiolysis impacts incurred in the reservoir ($Q_{reservoir}=Q_{total}-Q_{source}$).
v. Assessing the radiation dose rate ($dr_Q$=f(reservoir properties)) derived from the reservoir that is impinging on the reservoired fluids. This assessment is based on reservoir composition and rock and fluid properties.
vi. Assessing the fluid mixing processes impacting proxy distributions within the natural reservoir made using a reservoir radiolysis and mass transport compositional simulation tool.
vii. Calculating a reservoir fluid residence age (RA) or residence age profile from multiple samples, as:

$$RA = \frac{Q_{reservoir}}{dr_Q}$$

viii. Inverting the residence age profile to solve for net fluxes of petroleum into and within the reservoir, and out through the caprock, or from the spill points of the reservoir trap.

The aforementioned technologies, elements and steps, may be linked to determine the petroleum fluid residence age in a subsurface reservoir, or to determine a residence age profile (using multiple samples), in an approach that may involve:
i. The identification and accommodation of controlling parameters resulting in chemical changes related to radiolysis in the rock/fluid system.
ii. The identification of appropriate radiolysis proxies and measurement of the radiation susceptibility of each proxy type.

iii. Determination through experiments for each petroleum type, of the quantitative impact of all of the parameters affecting the radiation alteration of reservoir fluids.

iv. Determination of the quantitative interaction among the controlling variables of petroleum radiolysis, including petroleum chemistry, bulk fluid (water, oil, gas) properties, physical properties of the source and reservoir (including density, porosity, oil saturation), and reservoir lithology including effective radionuclide concentrations and nominal radius of net gamma radiation impact.

v. The ability to separate the effects of petroleum radiolysis in the parent source rock from petroleum radiolysis in the final hosting reservoir.

Sampling Well Test, Production or Reservoir Core Fluids to Create a Sample Set for Analysis Appropriate samples can include well test and production fluid samples, fluid samples obtained using borehole sampling devices such as MDT, RFT, DFA systems, and also reservoir core or sidewall core or cuttings samples which contain reservoir fluids and where the fluids can be removed from the rock medium using physical methods (centrifugation, compaction), or chemical methods such as solvent extraction.

A method is provided for selecting sampling locations, which may involve assessing samples in close proximity, i.e. proximate samples from proximate sampling locations, (e.g. sampling within approximately 1 m, 2 m, 3 m, 4 m, 5 m, 6 m, 7 m, 8 m, 9 m, 10 m, 15 m, or 20 m, for example), to any distinct more (or less) radioactive local environment in the surrounding geological setting and assessing any potential contamination. An example would be a more radioactive than average reservoir sections such as the reservoir material adjacent to a "hot" shale as indicated on a gamma ray log. Sampling petroleum-free ("non-stained"), reservoir intervals may also be useful to assess the impacts of any sample contamination related to oilfield activities and the impacts, for example, of oilfield fluids such as drilling muds. Petroleum samples from production, production tests or formation tests, in which the sampling strategy is defined based on other technical requirements can also be used.

Solvent or chemical extract samples from non-oil-stained cores can also be used to assess background radiolysis proxy contamination. Such assessments will assist in the selection of radiolysis proxies used in the method. For example, if an oil-based drilling mud may be used during drilling operations and such fluid is found to have contaminated the sample, any proxies found in the drilling fluid may be either excluded from the application or the samples may be cleaned physically and/or chemically to remove contaminating species, or by using an analytical approach such as liquid chromatography to separate a targeted non-contaminated sub-fraction of the fluid for analysis of proxy abundance. In some embodiments, proxies will be chosen which are not present in likely contaminants such as drilling muds, test cushion fluids or well work over fluids.

Identifying and Selecting Radiolysis Proxies

A method is provided to identify potential radiolysis proxies based on laboratory petroleum irradiation experiments, to assess the susceptibility of individual petroleum and individual petroleum components to radiolysis, their concentration in the petroleum, and the ease of analytical detection and measurement of these individual petroleum components (skillful selection of analytical techniques). Appropriate radiolysis proxies may also be defined based on their resistance to in-reservoir alteration processes such as biodegradation.

A series of different petroleum or other organic species may be subjected to laboratory irradiation experiments, which involves the exposure of samples to ionizing irradiation followed by subsequent analysis of the compositional alterations. Samples may be transferred to a suitable sample container. These may be inert or predictably reactive to gamma irradiation and may be capable of isolating and retaining headspace gases under pressure. They may be selected so as to not contribute to, or remove, chemical proxies of radiolysis from the sample material during the irradiation or subsequent storage components of the method. Flame sealed glass ampoules and/or polymer septum sealed glass vials, have been demonstrated to be suitable and may be sealed under an atmosphere of choice. In some implementations, relatively inert gases such as argon may be used, but other gases or mixtures can be used. Chemical inertness, as typically characterized, does not necessarily indicate inertness under gamma radiolysis and some chemically inert media such as nitrogen gas may become chemically active when irradiated. Samples can also be irradiated while in containers exposed to the atmosphere. The sample may or may not be spiked with stable internal standard compounds to enable subsequent quantitative analysis of targeted chemical proxies, but internal standards for quantitation purposes are usefully added to the samples after irradiation has been carried out.

Water, brine, or other fluids or reservoir solids such as appropriate minerals (e.g. quartz, calcite, clay minerals), can be added for the purpose of mimicking the complete natural subsurface conditions. Whole reservoir samples can also be irradiated. This approach also allows the determination of the impact of reactive oxygen species from water radiolysis on the overall radiolysis process.

In some implementations, solid material such as organic rich sedimentary rocks such as source rocks, containing solid organic matter in its pores can be used to calibrate in-source radiolysis processes.

By carrying out a variety of irradiation experiments with different total doses, a sample set with varying accumulated radiation doses is generated. For purposes of the present Examples, a particular sample holder and irradiation system was developed which permits samples to be simultaneously irradiated at a variety of total doses at the same time. An indexed sample holder for radiolysis experimentation, essentially transparent to gamma radiation, enables accurate placement of samples in a well constrained heterogeneous radiation field, enabling irradiation of large numbers of samples at different total doses, across a calibration range quickly over a range of total dose loadings.

The amount of organic material to be irradiated can vary widely, for example from less than 1 mg to 10 s of g depending on sample holder and irradiator configuration. Samples are irradiated to multiple, pre-defined radiation doses, for example using gamma ray photons with an energy between 0.5 and 2.5 MeV, at dose rates ranging from 0.01 Gy/h to 20 Gy/h, generating a set (4 samples minimum) of irradiated samples ranging from 0-1000 kGy. In alternative implementations, X-rays can also be used. The gamma ray sources are typically readily available radioactive metal elements such as isotopes of cobalt or cesium, but other physical devices can also be used to irradiate samples with gamma radiation.

In some implementations, the analytical methods used to measure radiation proxy formation and/or degradation are a combination of gas chromatography, mass spectrometry and/or spectroscopic methods such as infrared, nuclear magnetic resonance, UV/Vis and fluorescence spectrometry, electron paramagnetic resonance (EPR) or electron spin resonance (ESR) spectroscopy may also be used. Thin layer chromatography or other liquid chromatography methods can be used to produce a concentrated analyte fraction containing the targeted proxies prior to instrumental analysis. Other methods developed include the compositional and carbon, hydrogen, oxygen, sulfur or other elements, stable isotopic analysis of the gases, liquid or solid species produced during radiolysis.

Chemical derivatization approaches to detect radiolysis products at low levels, such as derivatization of carbon-carbon double bonds produced during radiolysis with chromophores that can be sensitively detected with fluorescence spectroscopy can also be used in some implementations. Alternative methods to measure proxy concentrations at low concentration levels include, for example, compound specific solid-state sensors including electronic noses, FTMS, immunological methods, chromophore tagged fluorescence-based methods.

Analysis of proxy concentrations and distributions may be carried out using analytical methods capable of distinguishing the intact sample signal from any contaminant background signature. This may involve separation schemes such as chromatography to produce sub-fractions free of contaminant signals.

The determination of proxy concentrations may include the addition of internal standards, and the analysis of blanks and control samples, so as to avoid artifact effects and to detect contamination and other procedural issues. One example of a select implementation is the use of proton or carbon nuclear magnetic resonance to analyze carbon-carbon double bond systems produced pervasively during petroleum radiolysis, throughout an entire petroleum sample.

In addition to determination of the composition and concentration of radiolysis proxies produced during petroleum sample irradiation, chemometric methods such as principal components analysis, partial least squares, factor analysis, or machine learning approaches for data analysis can also be used to assess specific or gross chemical changes in a petroleum sample in response to a radiation dose, assessed using a single or assemblage of analytical approaches. Using such approaches, proxies can be identified and then used for reservoir fluid age dating in the manner described herein.

A method is provided to measure the radiolysis susceptibility of petroleum constituents, which involves determining the quantitative response of specific components in a petroleum to progressively increasing radiation doses. Quantitative response may be determined by measuring the chemical and/or stable isotopic composition of a sample exposed to different laboratory accumulated radiation doses at dose levels comparable to those commonly experienced by petroleum reservoirs over geological timescales. Because the radiolysis susceptibility of petroleum components is dependent on the overall petroleum chemistry and especially the ratio of saturated to aromatic carbon skeletons in the petroleum sample and the molecular weight range of the petroleum species, a sample-specific calibration protocol to determine response to irradiation may be used.

The radiolysis susceptibility by compound may be defined as the linear, or sub-linear, quantitative relationship between the concentration of a compound, or group of compounds in the sample, and the incurred radiation dose, normalized to the initial concentration of that component in the parent petroleum. The radiolysis susceptibility of a range of compounds in the petroleum, may be used as an input for selection of the proxies most applicable to the specific fluid residence age measurement application.

The evolution of proxy concentrations with different radiation doses may be measured based on the concentration change as a function of accumulated dose in a series of experimental irradiation tests whereby several aliquots of crude oil are exposed to a range of total gamma ray doses and then the resulting crude oils are analyzed using one of the analytical methods described herein. The radiolysis susceptibility is calculated as the proxy's slope of concentration change with dose, divided by its initial concentration. The radiolysis susceptibilities of different petroleum species in many oils have been identified. FIG. 1 illustrates the distribution of radiolysis susceptibility of monitored compounds, as grouped by compound class, for AHO (red) and NSO (blue) irradiated crude oil sets. The AHO oil is a biodegraded heavy oil, the NSO oil is a light, high API marine crude oil samples. The gamma ray radiolysis susceptibility ($kGy^{-1}$) of the different compounds is derived by normalizing the gradient (slope), for each compound, in the linear trend of compound concentration versus radiation dose, to the compounds original concentrations in the parent oil, for each monitored chemical compound or class. TAS=triaromatic steroid hydrocarbons, MAS=monoaromatic steroid hydrocarbons, TT=tricyclic terpanes. On the box plot, maximum and minimum values for each compound class are represented by whiskers, while the top and bottom of the boxes represent first and third quartiles of the data.

A few examples of the most sensitive radiolysis specific species for measurement in terms of concentration decrease with increasing radiation dose (degradation proxies) are long chain n-alkanes present in abundance in crude oil, biomarker alkanes, pristane, phytane, hopane, $C_{30}$ sterane, $18\alpha$(H)-22,29,30-trisnorneohopane (Ts), $17\alpha$(H)-22,29,30-trisnorhopane (Tm). Polar compounds such as alcohols, phenols, carboxylic acids have also been identified as being destroyed during radiolysis.

A second group of proxies which are species produced during radiolysis of a petroleum (production proxies), includes the production of carbon-carbon double bonds (alkenyl carbon), in several alkylated petroleum fractions (aliphatic hydrocarbons, alkylated aromatic hydrocarbons and alkylated hetero compounds including nitrogen, oxygen, sulfur, metals and other elements other than carbon and hydrogen), low molecular weight n-alkanes, light hydrocarbons including hydrocarbon gases, and high molecular weight products produced by bimolecular addition reactions. Other production proxies include the production of hydrocarbon gases with isotopically depleted carbon isotopic signatures present.

Polar non-hydrocarbon compounds derived from reactions between petroleum components and reactive oxygen species generated from water radiolysis have also been identified.

Diamondoid hydrocarbons have shown enhanced resistance to radiolysis alterations (i.e. low radiolysis susceptibility). Some proxy compounds, such as intermediate carbon number range n-alkanes, in the carbon number range $C_{8-14}$ for example, exhibit a more complex response whereby they are both generated by radiolytic destruction of longer chain hydrocarbons and undergo subsequent penecontemporaneous radiolytic destruction themselves. Analysis of the concentration of these species requires a multicomponent radiolysis kinetic model.

Multiple proxies can be combined in this assessment, including combinations of both destruction and production-based radiolysis proxies to assess radiation dose experienced by a petroleum sample.

A method is provided to select the radiolysis proxies for use in the techniques disclosed herein. For proxies based on the destruction and reduction in concentration of individual compounds or groups of compounds (degradation or "radiodegradation" proxies), this involves selection of a range of compounds with large negative radiolysis susceptibilities that are present in crude oils in relatively high abundance. For proxies based on the production of new species (radiosynthesis proxies), this involves selection of a range of compounds or detectable functional groups, absent initially in the primary petroleum charged to an oilfield, or present in very low concentrations prior to emplacement in a petroleum reservoir, which have large positive radiolysis susceptibilities and are thus produced in increasing quantities with increasing radiation dose and radiolysis.

A factor in the choice of radiolysis proxies for a given application, is their resistance to common in-reservoir petroleum alteration processes such as, for example, biodegradation which commonly affects most natural petroleum accumulations present in sedimentary basins at depths shallower than a few kilometers. Resistance to biodegradation of individual compounds, depends on the actual net level of biodegradation in the sample petroleum and the compound type. Biodegradation resistance at low and moderate levels of biodegradation is found in high molecular weight cyclic alkanes, such as hopanes or steranes, alkylated polycyclic hydrocarbons and alkenyl carbon in high molecular weight alkylated aromatic species or in alkylated hetero compound fractions including the resins and asphaltenes. An advanced biodegradation level scale to assess which species would be appropriate as reservoir age radiolysis proxies can also be used. An example of such scales would be the Peters and Moldowan or the Manco biodegradation scale (Peters and Moldowan, 1993; Larter et al., 2012). Biodegradation resistant production proxies are also found in high molecular weight and alkylated aromatic compounds where they may contain oxygen derived from reactions between petroleum components and reactive oxygen species associated with water radiolysis. Examples include, but are not limited to, biodegradation resistant cyclic, alcohols, epoxides, ethers, aldehydes, ketones, carboxylic acids, furans, quinolines, phenols.

Assessing the Total Natural Radiation Doses ($O_{total}$) Experienced by Petroleum Fluids in Natural Reservoirs.

A method is provided to assess the total natural radiation dose ($Q_{total}$) experienced by petroleum fluids in natural reservoirs, which involves measuring the concentrations and distributions of the targeted radiolysis proxies and interpreting those concentrations in terms of natural radiation dose using a matrix-specific proxy calibration relationship with incurred radiation dose, the sample specific radiation susceptibility measurement for that proxy type, in that specific petroleum.

Any petroleum sample is expected to exhibit some level of naturally accumulated radiation dose, even if to a minor extent, which would be evident in terms of a measurable quantity of a radiolysis proxy in the sampled petroleum.

Figure 2:
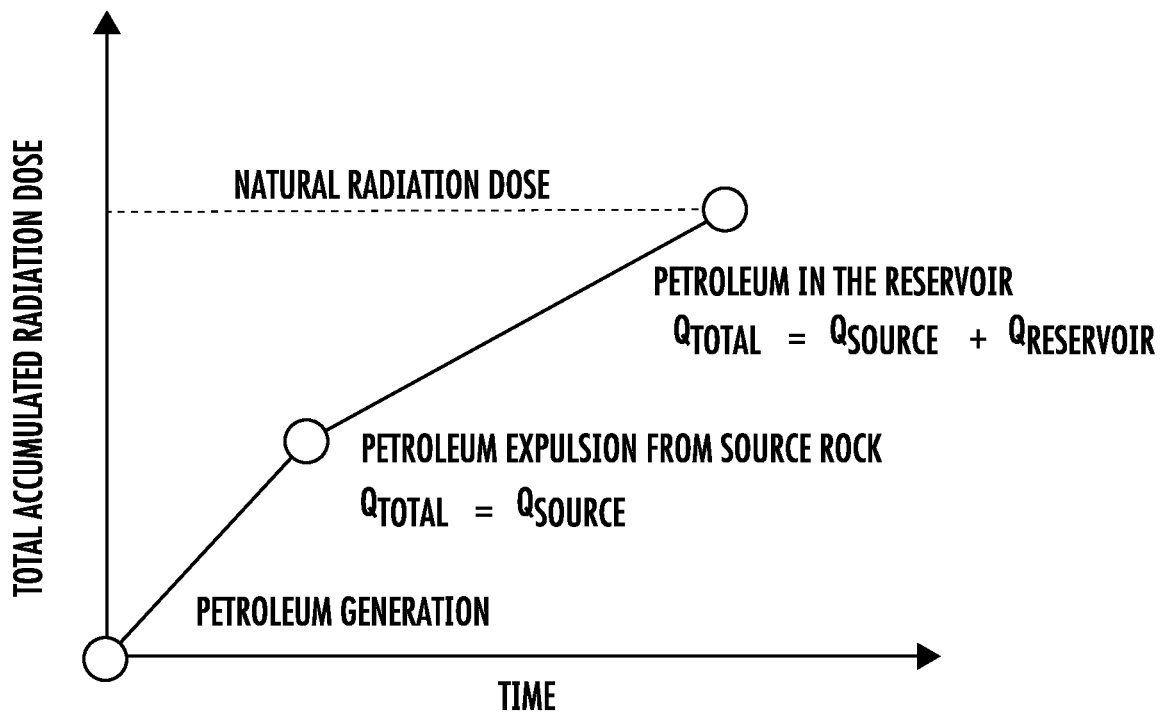
FIG. 2 is a schematic illustration of the evolution of the total natural radiation dose accumulated as the petroleum fluid migrates away from the source rock and is trapped in a reservoir for a given amount of time.

FIG. 2 exemplifies how $Q_{total}$ evolves in a petroleum system and shows a cross plot of a schematic irradiation history for organic matter in a petroleum system as it moves from the source rock, through to the reservoired petroleum. With time, petroleum generating organic matter, and free petroleum, both in the source rock and in the reservoir rock, accumulates radiation dose and undergoes chemical change. Part of this dose accumulates in the source rock between the time of petroleum generation and the time of petroleum expulsion. Some radiation dose impacts may also accumulate in a petroleum sample during the process of migration from source rock to a trap, though commonly this transport process happens rapidly on a geological timescale and this incremental dose may be quite small. Finally, in the reservoir rock the petroleum accumulates a further incremental radiation dose. In most petroleum systems the carrier bed irradiation derived dose would be minimal and might in many cases be ignored.

Figure 3:
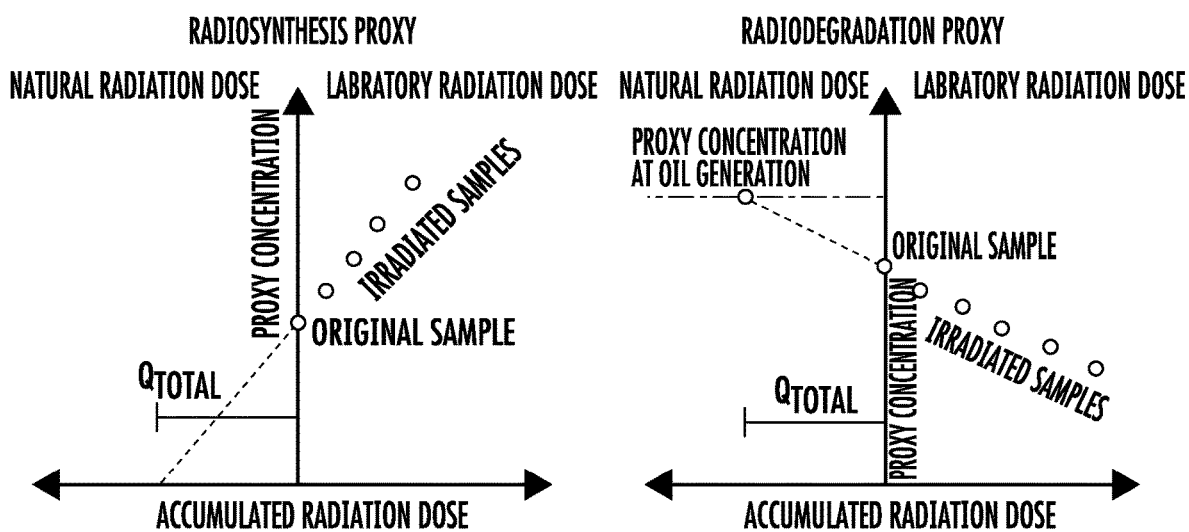
FIG. 3 is a schematic representation of natural radiation dose estimates based on selected proxies and sample-specific irradiation experiments.

FIG. 3 shows how measurements of proxy concentration in both the natural sample petroleum, combined with measurements of the proxy concentrations in the artificially irradiated sample suite at different added radiation doses, can be plotted to enable the determination of the natural accumulated radiation dose absorbed by a petroleum in the subsurface.

The total natural dose encountered by the petroleum in the reservoir is determined by plotting a regression line of proxy concentration versus additional, in laboratory, irradiated dose for the artificially irradiated samples, together with the analysis of the native reservoir sample petroleum. In the case of a compound produced in proportion to increasing radiation dose, fitting a line to the data from the native sample and the artificially irradiated samples, allows the user to back extrapolate the curve of proxy concentration versus accumulated radiation dose, to a zero proxy concentration. The slope of the line relating radiation proxy concentration and incurred radiation dose indicates the sensitivity and matrix behavior of that individual petroleum and radiation dose proxy compound suite. By measuring the radiation dose proxies in the irradiated samples and in the native sample, fitting a line to the dose versus proxy concentration data permits both the determination of the radiolysis susceptibility of the proxy compound (related to the slope of the line of concentration versus dose), and also the back extrapolation of the radiation dose proxy concentration to zero initial radiation dose.

In the case of degradation proxies, where the compound concentration decreases systematically with increasing radiation dose, the intercept of the proxy concentration and the extrapolated line then provides the estimate of the $Q_{total}$ for the petroleum sample as the modulus of the intercept value. The proxy concentrations are estimated using geochemical assessments of the parent source rock, or analysis of reservoirs within, or close to the parent source rock. In some implementations, ratios of compounds and/or isotopic signatures of selected proxies are used as radiolysis proxies.

In the case of radiosynthesis proxies, where compound concentration or functional group concentration increases with increasing radiation dose, the intercept of the extrapolated line and the accumulated radiation dose axis (i.e. zero proxy concentration) then provides the estimate of the $Q_{total}$ as the modulus of the intercept value. In some implementations where the radiosynthesis proxy is not zero at the time of the oil entering the reservoir, such initial value must be accounted for.

In some implementations, once the sample-specific proxy production (radiosynthesis or production proxies) and/or degradation (radiodegradation or degradation proxies), rates ($s_{proxy}$) with increasing radiation dose, are determined using the radiolysis susceptibility information, the total natural dose ($Q_{total}$) of the sample can be determined using the proxy signal measured in the original sample ([proxy]) as:

$$Q_{total} = \frac{[proxy]}{s_{proxy}}$$

Alternatively, the incurred natural doses in the sampled petroleum can be directly assessed by inspection of the x-axis intercepts, as indicated in FIG. 3. In some implementations, prior proxy response/radiation dose calibrations constructed using different but similar samples can be used to derive the sample response to radiation and the total radiation dose of the original sample in new sample suites. It is acknowledged that the rates of proxy radiosynthesis and radiodegradation of individual chemical moieties are very sensitive to the overall sample chemical composition, which may limit the use of non-sample specific calibration sets, thus ideally the method requires sample specific calibration protocols as described previously.

The incurred natural radiation doses experienced by petroleum fluids in natural reservoirs are determined based on either one sample or on a multi-sample profile. Multi-sample profiles are preferred as they permit some of the methods above to be used in which the local dosing effects of highly radioactive reservoir intervals can be taken advantage of to derive $Q_{reservoir}$ and $Q_{source}$ from a measured $Q_{total}$.

Estimating in-Reservoir Radiation Dose ($Q_{reservoir}=Q_{total}-Q_{source}$).

A method is provided for decoupling the radiolysis impacts on petroleum in parent source rocks and reservoir rocks, thus deriving: $Q_{reservoir}=Q_{total}-Q_{source}$. Simply calibrating chemical compositional change to a radiation dose impact in a petroleum may be insufficient for a functional chronometric system. Multiple controlling properties and processes may be simultaneously evaluated to obtain a reliable result for a petroleum residence age assessment. Given the higher radionuclide concentrations in shales (common petroleum source rocks), versus for example, the typical sandstone or carbonate (e.g. limestone, dolomite) reservoir rocks, plus the commonly observed longer residence ages of organic matter (both primary source kerogens and any already generated petroleum), in source rocks, compared to reservoirs, the radiation dose experienced by pre-, or post-generation organic matter in a source rock may exceed that experienced by oil in a reservoir.

In one embodiment, the method can specifically decouple in-reservoir irradiation impacts from the accumulated irradiation dose while the petroleum fluid is generated at the source rock, for example by using radiosynthesis proxies that are not present in the petroleum leaving the source rock. In this case, the radiation dose calculated from the proxy analyzed in the reservoir is dominantly directly from in-reservoir radiolytic processes ($Q_{reservoir}=Q_{total}$).

Derivation of $Q_{source}$ can be made using several procedures. The first approach is to use natural suites of thermally matured source rocks of the type sourcing the target oil and analyze the petroleum within the source rock, and also in small collateral reservoirs (thin sandstones, siltstones or porous limestones) within or close to the source rock. The analysis of the radiolysis proxy of such source rock systems at different levels of thermal maturity provides a calibration curve for the primary petroleum charge at any thermal maturity level that the particular source rock system will deliver to the reservoir.

In some implementations, local in-reservoir gamma ray dosing signals, which vary through the reservoir in parallel with varying lithology and, in particular, shale content, are used as a reservoir radiation source signature that can also be examined in the hosted petroleum composition. The spatial profile of this in-reservoir signal will be unique to the reservoir radiation process and can be used to estimate the portion of the radiation dose from reservoir and source rock. This part of the present technology can for example be applied using a simple graphical method, which may be augmented by an advection diffusion simulator to assess mixing of radiolysis products within a crude oil column.

This approach to deriving $Q_{source}$, $Q_{reservoir}$ takes advantage of the observation that gamma rays, and associated Compton scattered electrons only travel short distances (~1 meter or less), within sedimentary rocks and thus cause locally influenced radiolysis impacts. That means that the in-reservoir radiation dose signal ($Q_{reservoir}$) will track the variation in in-reservoir gamma ray radiation dose rates delivered by the reservoir rock medium. This signal is derived at high spatial resolution from a borehole gamma ray log (either total gamma signal or spectral gamma signals combined). Gamma ray logs can have vertical resolutions as great as 30 cm. By graphically subtracting an affine scaled image of the borehole gamma ray log inferred radiation dose profile, near a section of reservoir containing both a more radioactive and a less radioactive interval, vertically within the reservoir section of interest, from the total reservoir dose profile inferred from the radiolysis proxy analyses as described above, permits the derivation of the local in-reservoir signal ($Q_{reservoir}$), and the $Q_{source}$ radiation dose signal inherited from the source rock.

Figure 4:
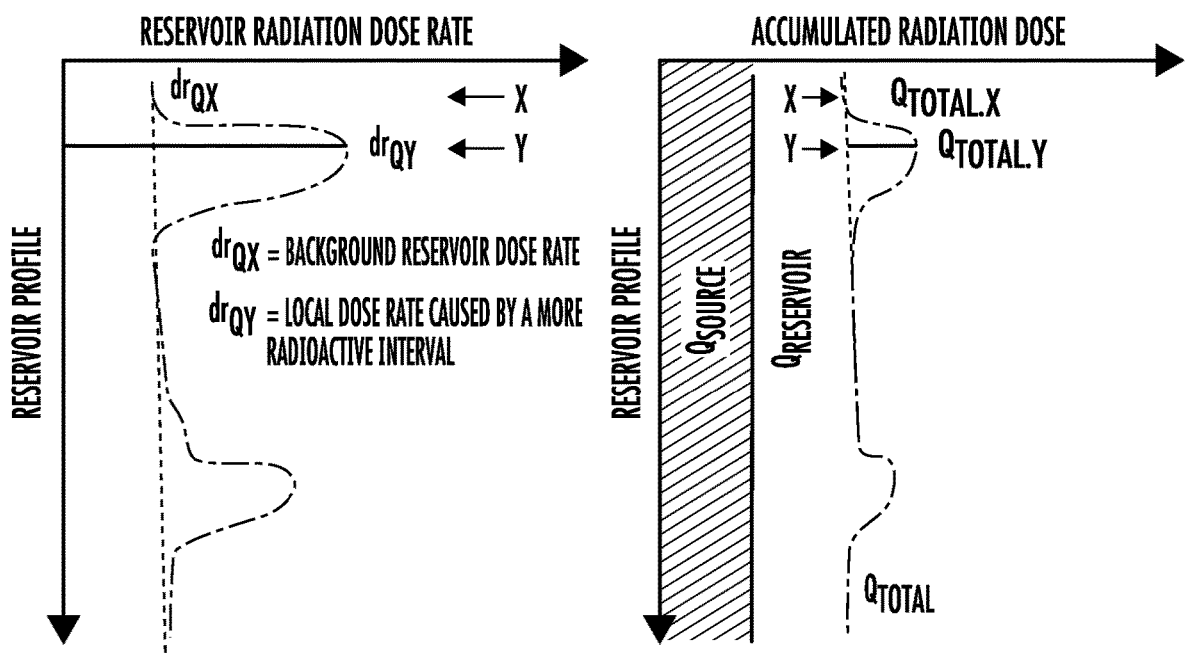
FIG. 4 is a schematic representation of the elements used in Qreservoir determinations, when the local in-reservoir gamma ray dosing signals track the variation in in-reservoir gamma ray radiation dose rates delivered by the reservoir rock medium.

Thus, as just one example of the approach, in FIG. 4, the right-hand pane shows the total radiation dose delivered to the reservoired petroleum, assessed using the radiolysis proxy approach described here. This total dose assessment reflects both radiolysis proxies carried into the reservoir from the source rock and the locally influenced radiolysis effects of the reservoir medium itself. Within the reservoir medium are two more radioactive intervals (likely more shale rich intervals), with higher gamma ray signals and thus higher radiation dose rates. Petroleum trapped near these more radioactive intervals experiences higher net radiation ray doses.

Assuming the concentration of source rock derived radiation dose proxy in the reservoired petroleum is approximately constant within a narrow range of reservoir depth, then the relative proportions of the total dose rate signal from the gamma-ray log near the shale and that found in a sample away from the shale allow us to calculate a scaling factor or ratio $$\frac{dr_{QY}}{dr_{QX}},$$

for near snare dose rare versus the more background reservoir dose rate. As gamma-ray radiation dose is quite local, and assuming the same residence age (RA) for fluids within the interval comprising positions Y (higher gamma-ray dose rate) and X (background gamma-ray dose rate), we can then use the chemical proxy total dose estimate $Q_{total}$, and the scaling factors from the gamma ray log to determine the in-source radiation dose ($Q_{source}$) incurred as RA at position X = RA at position Y $$\frac{Q_{reservoir.X}}{dr_{QX}} = \frac{Q_{reservoir.Y}}{dr_{QY}}$$

$$\frac{(Q_{total.X} - Q_{source})}{dr_{QX}} = \frac{(Q_{total.Y} - Q_{source})}{dr_{QY}}$$

$$Q_{source} = \frac{\left(\frac{dr_{QX}}{dr_{QY}}\right) * Q_{total.Y} - Q_{total.X}}{\left(\frac{dr_{QX}}{dr_{QY}}\right) - 1}$$

Measuring $Q_{total}$ from the chemical proxy dose estimate and determining $Q_{source}$ as above, permits us to determine the value for $Q_{reservoir} = Q_{total} - Q_{source}$.

Simulation tools, as described herein, may allow a more detailed assessment of the values of $Q_{total}$ corrected for transport effects such as diffusion and advective mixing of proxies within the moving petroleum fluids.

Assessing the Radiation Dose Rate ($dr_Q$=f(Reservoir Properties)).

A method is provided to assess the radiation dose rate from the reservoir that is absorbed by the reservoired fluids, inferred as a function of the reservoir properties.

Experimental assessment of the attenuation behavior of minerals and fluids in rocks, indicates it is gamma rays and the associated scattered electron avalanche that are the key radiolysis agents for petroleum in pore systems, as primary alpha and beta particles are commonly stopped within the mineral grains. The absorbed radiation dose received by the pore fluid is a complex function of radiation type, location of the fissioning radionuclides, and the effects of attenuation of different radiation types by the host reservoir medium. The attenuation depends on quantitative consideration of the concentration of the primary radionuclide, the lithology of the source and reservoir rock, the porosity and the oil and water saturation, and the density and composition of the reservoired fluid itself.

The radiation emission dose rate of the host geological setting is principally determined by the concentration of $^{238}$U, $^{232}$Th and $^{40}$K, or any combination of these and other major radionuclides present in the reservoir matrix. Radiation dose derived from a radioactive substance depends on the activity, or number of decays per unit time and can be estimated from the gamma ray or other high-energy radiation responses measured by well logging tools, for example the gamma ray logs, measured in API units.

The total energy released during radioactive decay, ultimately ends up as heat generated within the rock volume. Thus, there is a good correlation between gamma ray log responses, as an indicator of radioactive decay and total radiogenic heat production measured in sedimentary rocks. A correlation between gamma ray log responses for a reservoir unit (in API units) and radiogenic heat production measured for various sedimentary rock sections was published by Bücker and Rybach (1996), as:

Heat Generation($\mu W/m3$)=0.0158($GR[API]$-0.8)

where GR[API] is the gamma ray log response in API units. We can use such a relationship to relate the gamma ray log response to the total energy generated and absorbed within a local rock volume which is locally derived and ultimately converted by interaction with the reservoir medium as heat.

Only a fraction of the emitted high-energy radiation is effectively absorbed by the pore fluids themselves (i.e. oil, water and gas) in geological settings. Calibration factors are used for assessing the net effective radiation impacts on fluids and pore systems, from analysis of both reservoir medium and pore fluid properties and by using calibration experiments in the laboratory.

To convert total reservoir dose assessed using gamma ray log activity into an effective dose rate absorbed by the sample fluids, the present methods may use determinations of oil and water saturation levels, fluid phase densities and viscosities, fluid gamma ray absorptivity coefficients, and the volume fraction of fluid pores filled in the reservoir, i.e. the porosity. The reservoir radiation dose rate, corrected for matrix properties and geometry, is calculated by multiplying the estimated radiation output from the gamma ray log correlations by correction factors related, but not limited to, fluid saturation, phase densities, sample absorptivity coefficient and porosity. In some implementations, the absorbed radiation dose rate ($dr_Q$) is calculated as:

$$dr_Q = dr_{total} * \left(\frac{V_{petroleum} * \rho_{petroleum}}{\left(\begin{array}{c} V_{mineral} * \rho_{mineral} + \\ V_{water} * \rho_{water} + V_{petroleum} * \rho_{petroleum} \end{array}\right)}\right)$$

Where:

$dr_Q$ is the radiation dose rate absorbed by the petroleum fluid in a pore system.

$dr_{total}$ is the total radiation dose rate as estimated from gamma ray logs (see above).

$V_{petroleum}$ is the volumetric fraction of the petroleum phase in the reservoir medium, calculated as $V_{petroleum}=\Phi*S_0$, where $\Phi$ is the reservoir porosity and $S_0$ the oil saturation.

$V_{mineral}$ is the volumetric fraction of the mineral phase in the reservoir medium, calculated as $V_{mineral}=1-\Phi$, where $\Phi$ is the reservoir porosity.

$V_{water}$ is the volumetric fraction of the water phase in the reservoir medium, calculated as $V_{water}=\Phi*(1-S_0)$, where $\Phi$ is the reservoir porosity and $S_0$ the oil saturation.

$\rho_x$ is the density for the given phases (x=mineral, petroleum, water).

Calculating a Reservoir Fluid Residence Age (RA)

A method is provided to calculate a reservoir fluid residence age (RA) for a single petroleum sample, or residence age profile as:

$RA=(Q_{reservoir}/dr_Q)$

Analysis of multiple samples permits the development of a reservoir fluid residence age profile, which advantageously allows for correction of radiolysis dose estimates and assessment of fluxes of petroleum into and out of the reservoir.

Net Fluxes of Petroleum into and within the Reservoir from the Residence Age Profile.

Figure 5:
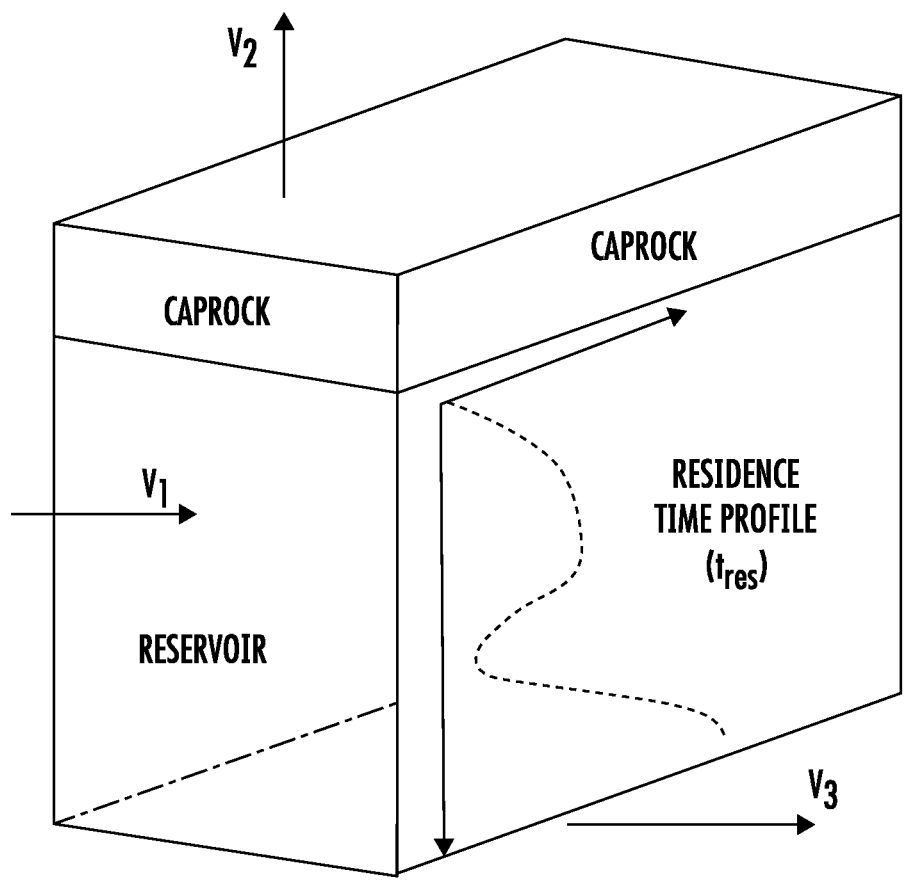
FIG. 5 is a schematic representation of fluid fluxes in and out of a reservoir and the resulting residence time profile.

A method is provided to invert the residence age profile to solve for net fluxes of petroleum into and within the reservoir, and out through the caprock, or from the spill points of the reservoir trap. When multiple samples are analyzed, the use of a geological timescale reservoir simulation tool coupling radiolysis proxy production or destruction, and fluid transport into and out of the reservoir, permits the use of the reservoir fluid residence age profile ($t_{res}$) to solve for net fluxes of petroleum into and within the reservoir ($v_1$) and out through the caprock ($v_2$) or from the spill points ($v_3$) (FIG. 5).

A compositional reservoir-basin modelling simulator may be used to simulate oil charge filling of a reservoir, the local impact of in reservoir radiation dose on crude oil composition through radiolysis, making allowance for the attenuation of the gamma radiation within the reservoir, and the resulting diffusion and advection of the radiolysis proxies within the reservoir throughout the reservoir fluids.

The numerical model may for example use a residence time predictive model based on crude oil radiolysis, that has interactions between oil phase and radiation, while oil is charging and filling and subsequently spilling or leaking from a reservoir. The calibrated evolving response of crude oil composition as a function of time to prescribed radiation dose rates (radiolysis susceptibilities) may be used to calculate the concentration of both production and destruction radiolysis proxies within the simulator.

The measured attenuation coefficients of gamma radiation in rocks may also be used in the simulator. The simulator can then fit the observed radiation dose proxy measurement profile throughout the reservoir fluid column to simulated profiles calculated using measurements of reservoir dose rate profile and various iterations of the charged, leaked and spilled oil fluxes (FIG. 5), estimated from basin modelling simulators. Using standard model fitting approaches the idealized fluxes are derived and optimal reservoir fluid residence ages determined from the collective data.

There are three material phases in the simulator: petroleum, water, solid (radioactive). There are n components in the model. The simulator can for example use any of the standard routes for reactive fluid flow simulation. Examples would be the use of a finite element or finite difference solvers to solve for simultaneous, charge of oil to a reservoir, diffusion of oil species within the reservoir fluid, radioactive decay and attenuation in the reservoir and irradiation of crude oil components to impact the radiolysis proxies, coupled to charging, leakage and spillage of oil. Comparison of model predicted proxy concentrations and those observed by analysis of the petroleum in the reservoir fluid column are used to constrain the various model iterations and derive a "best model", optimized solution.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Terms such as "exemplary" or "exemplified" are used herein to mean "serving as an example, instance, or illustration." Any implementation described herein as "exemplary" or "exemplified" is accordingly not to be construed as necessarily preferred or advantageous over other implementations, all such implementations being independent embodiments. Unless otherwise stated, numeric ranges are inclusive of the numbers defining the range, and numbers are necessarily approximations to the given decimal. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification, and all documents cited in such documents and publications, are hereby incorporated herein by reference as if each individual publication were specifically and individually indicated to be incorporated by reference herein and as though fully set forth herein. The invention includes all embodiments and variations substantially as hereinbefore described and with reference to the Examples and drawings.

EXAMPLES

In the example shown below, the generation of carbon-carbon double bonds within the petroleum chemical matrix with increasing radiation dose, is used as a radiosynthesis proxy.

Methods as disclosed herein may be used to assess petroleum charge times and rates, key variables in hydrocarbon prospectivity that may be used to define volumes of trapped petroleum and the dynamics of trap integrity, including leakage and alteration phenomena. Knowledge of the timing of reservoir trap and seal development relative to the migration of crude oil facilitates exploration success. For example, in one specific case a forward basin model in which the reservoir rock was ~150 million years old, both suggested petroleum generation and reservoiring occurred about 60-75 million years ago. This model provided erroneous predictions, which were tested during subsequent drilling, that were in contrast to the expected exploration results. An alternative but otherwise unconstrained migration model that was subsequently developed to explain the drilling results in the area was independently confirmed using the technology disclosed herein which showed that the timing of the emplacement of petroleum within the reservoir (≤18 million years) was much later than the time of initial petroleum generation.

Example 1: Disparate Samples

A crude oil sample set, comprised of well test fluids, is used in this example, illustrating that the present methods may be applied to a disparate range of samples. The sample and reservoir properties are as follows.

| Sample | Sample density (g/cm³) | Reservoir GR_LOG response (API) | Porosity (%) | Oil Saturation (%) |
|---|---|---|---|---|
| A | 0.841 | 15 | 12.1 | 72.7 |
| B | 0.832 | 30 | 13.3 | 71.9 |
| C | 0.860 | 165 | 10.0 | 25.0 |
| D | 0.894 | 60 | 29.0 | 89.0 |

Samples were irradiated according to the method, at total dose levels close to those experienced by crude oils over geological time in typical sandstone reservoirs, with total doses in the range of 0-120 kGy.

An irradiator with a $^{137}Cs$ source, was used for the gamma ray irradiation experiments. The sample holder was constructed with styrofoam to accommodate up to 48 glass ampoules (1 mL or 2 mL vials).

To determine the radiation dose rates for individual samples within the sample holder, the radiation dose rate for each sample spot was calibrated individually. Sample spots were filled with a water-based gel to mimic oil density, and GAFchromictm EBT3 radiochromic dosimetry film (0.5×2 cm) was placed inside the gel-filled spots. Independent 2-minute irradiation tests were performed in triplicate, and the films subsequently digitized using an Epson 10000XL professional scanner. Densitometry using the red channel was used to evaluate the radiation dose absorbed by each sample spot.

Samples were prepared for the irradiation experiments by placing approximately 1 g of material in 1 mL glass ampoules, which were then flame-sealed under argon and placed in a custom sample holder. The number of samples and the applied radiation doses are described in the table below.

| Sample | Laboratory radiation dose range (kGy) | Irradiated ampoules |
|---|---|---|
| A | 10.4-80.4 | 3 |
| B | 13.5-125.5 | 6 |
| C | 10.0-91.2 | 4 |
| D | 13.7-122.5 | 4 |

After the irradiation experiments, irradiated samples were taken from the ampoules and analyzed by $^1$H NMR. A Bruker NMR spectrometer operating at 600 MHz was used for $^1$H NMR analysis of original and irradiated samples. Experimental conditions include: 4100 scans, relaxation delay=2 s, acquisition time=3.89 s, filter width=125 kHz, sweep width=8400 Hz, flip angle=30°, sample rotation=20 Hz. Whole oils were diluted to approximately 200 mg/mL in $CDCl_3$. Spectra baselines were manually corrected with points selected in regions free of peaks and also at the regions of interest. Olefinic hydrogen ($H_{ole}$, δ 6.3-4.2 ppm) area is measured in relative terms as $H_{ole}/(H_{aro+sat+ole})$, where aromatic ($H_{aro}$) and saturated ($H_{sat}$) hydrogen chemical shift ranges are δ 8.3-6.6 and δ 3.5-0.1 ppm, respectively.

The advantage of NMR spectroscopy over an analytical method such as GC-MS, is that functional groups such as carbon-carbon double bond environments can be detected and quantitated, irrespective of their chemical location in a complex mixture of many chemical species. Thus, whole oil samples can be analyzed intact.

Figure 6:
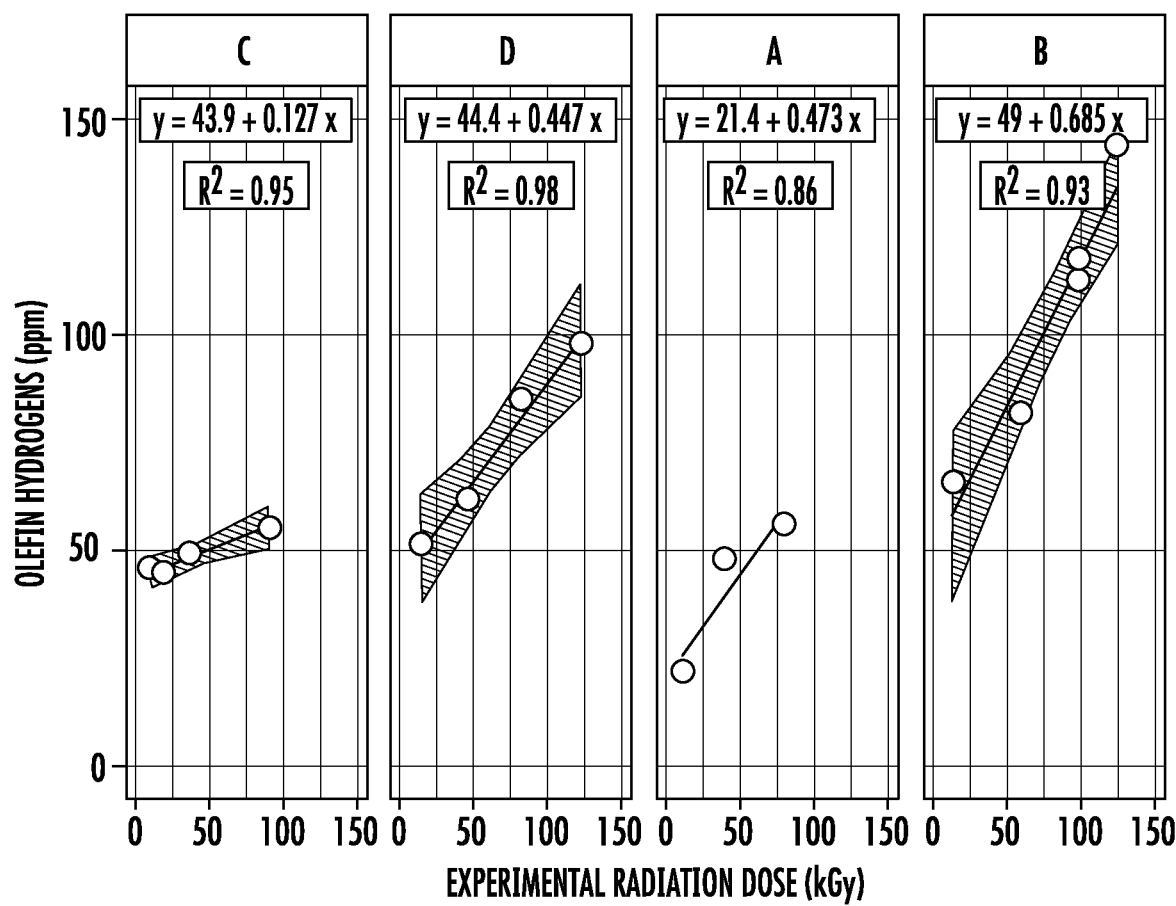
FIG. 6 is a series of four graphs, illustrating an increase in carbon-carbon double bonds after laboratory irradiation experiments, measured as olefinic hydrogens detected in $^1H$ NMR experiments.

By fitting a linear model to the cross plot of the carbon-carbon double bond content versus laboratory radiation dose, the rate of proxy formation with dose (slope of the proxy concentration versus radiation dose line) is obtained, as illustrated in FIG. 6.

The original oils are also analyzed in terms of their carbon-carbon double bond content and the total natural radiation dose $Q_{total}$ is calculated dividing them by the slope ($s_{proxy}$). The table below shows the calculated $Q_{total}$ (kGy) for this sample set.

| Sample | $s_{proxy}$ (ppm/kGy) | $R^2$ | $Q_{total}$ (kGy) |
|---|---|---|---|
| A | 0.47 | 0.86 | 34.3 |
| B | 0.69 | 0.93 | 145.5 |
| C | 0.13 | 0.95 | 563.8 |
| D | 0.45 | 0.98 | 72.5 |

Based on the petroleum system studies in this example, it is assumed that there is no other source of carbon-carbon double bonds contributing to the fluid composition beyond radiolysis. Previous experimental work revealed that there is no proxy contribution from drilling fluids or from the parent source rocks. In such cases, $Q_{total}=Q_{reservoir}$.

In this context, we note that we have analyzed olefin proxies in solvent extracts of source rocks at different thermal maturation stages. Indeed, proxy signals can be detected at different levels in such sample sets. One striking observation is that, at the beginning and throughout the oil generation window, olefin levels in the extracts are significantly lower compared to olefin-rich immature shales, which are likely carrying compositional features from precursor molecules input into the original source rock organic material at deposition. This disappearance of olefinic structures during the oil generation stage, is evidence of kerogen- and oil-cracking reactions taking place in the source rock, which can promote the hydrogenation of any carbon-carbon double bonds that may exist in the material. Thus, in applications with olefin proxies, it may in some cases be feasible to assume that fluids leave the source rock 'olefin-free', so that there is no need to correct for $Q_{source}$ in such embodiments.

Dose rates provided by the reservoir medium, may be calculated applying the formula given above. The residence age (RA, in Ma) is then calculated by dividing the $Q_{reservoir}$ by the local dose rate, as shown above.

| Sample | $dr_Q$ (kGy/Ma) | $Q_{reservoir}$ (kGy) | Residence age (Ma) |
|---|---|---|---|
| A | 1.4 | 34.3 | 23.9 |
| B | 2.9 | 145.5 | 50.5 |
| C | 15.8 | 563.8 | 35.6 |
| D | 5.8 | 72.5 | 12.6 |

Example 2: Determining Residence Age Variation

In the example shown below, the generation of carbon-carbon double bonds within the petroleum chemical matrix with increasing radiation dose, is also used as a radiosynthesis proxy. Three oil samples produced from different depth intervals, in the same sandstone reservoir, were used. The reservoir properties are essentially the same across the intervals where the samples were taken, as well as the recovered fluid properties.

The same methods and assumptions as in Example 1 have been applied and results are shown in the table below. A residence age variation of 4.5 Ma years, in this case, can be considered to fall within the overall method uncertainty.

| Sample | Sample density (g/cm³) | Reservoir GR_LOG response (API) | Porosity (%) | Oil Saturation (%) | $s_{proxy}$ (ppm/kGy) | $dr_Q$ (kGy/Ma) | $Q_{reservoir}$ (kGy) | Residence age (Ma) |
|---|---|---|---|---|---|---|---|---|
| E.1934m | 0.8941 | 65 | 21.0 | 55.0 | 0.43 | 6.3 | 95.3 | 15.0 |
| E.1942m | 0.8941 | 65 | 21.0 | 55.0 | 0.43 | 6.3 | 108.2 | 17.1 |
| E.1955m | 0.8941 | 65 | 21.0 | 55.0 | 0.43 | 6.3 | 80.2 | 12.6 |

Example 3: Correction for $Q_{Source}$

In this example, two oil samples recovered from different intervals of the same reservoir have been analyzed in terms of their $Q_{total}$. Differently than in Example 2, the reservoir is heterogeneous, and the samples were recovered from sections with distinct radiation dose rates, <5 meters apart from each other. The baseline gamma-ray log of the reservoir is 55 API units, but in some intervals, it can reach up to 105 API units.

| Sample | Reservoir GR_LOG response (API) | $dr_Q$ (kGy/Ma) | $Q_{total}$ (kGy) |
|---|---|---|---|
| F.1 | 55 | 6.1 | 852.5 |
| F.2 | 85 | 9.5 | 1227.3 |

The method described above is then used to calculate $Q_{source}$ $$Q_{souuce} = \frac{\left(\frac{dr_{QF.1}}{dr_{QF.2}}\right) * Q_{total.F2} - Q_{total.F1}}{\left(\frac{dr_{QF.1}}{dr_{QF.2}}\right) - 1}$$

$$Q_{source} = \frac{\left(\frac{6.1}{9.5}\right) * 1227.3 - 852.5}{\left(\frac{6.1}{9.5}\right) - 1} = 180.0 kGy$$

The residence age of both F.1 and F.2 fluids (assumed to be equivalent) is then calculated:

$$RA.F1 = \left(\frac{Q_{total.F1} - Q_{source}}{dr_{QF.1}}\right) = \frac{(852.5 - 180.0)kGy}{6.1 kGy/Ma} = 110.2 Ma$$

$$RA.F2 = \left(\frac{Q_{total.F2} - Q_{source}}{dr_{QF.2}}\right) = \frac{(1227.3 - 180.0)kGy}{9.5 kGy/Ma} = 110.2 Ma$$

Note that if the $Q_{source}$ is neglected, the residence age of samples F.1 and F.2 would be calculated as 139.7 Ma and 129.1 Ma, respectively. This highlights the importance of $Q_{source}$ correction in applications where radiolysis proxies in fluids may carry signal from the source rocks, although this may not be necessary as shown in Examples 1 and 2.

REFERENCES

Bailey D., van Aswegen A., Todd-Pokropek A. and Humm J. eds. (2015) *Nuclear Medicine Physics: A Handbook For Teachers and Students*. 1st ed., International Atomic Energy Agency.

Larter S., Oldenburg T., Marcano N., Snowdon L., Adams J. and Chanthramonti K. (2012) New routes to solutions of the WCSB oil charge conundrum: γ-ray Photons and Fourier Transform Mass Spectrometry. In *GeoConvention 2012: Vision Calgary*. pp. 1-6.

Frolov E. B., Melikhov V. A. and Vanyukova N. A. (1998) Olefins of radiogenic origin in crude oils. *Org. Geochem.* 29, 409-420.

Curiale J. A. and Frolov E. B. (1998) Occurence and origin of olefins in crude oils. A critical review. *Org. Geochem.* 29, 397-408.

Frolov E. B. and Smirnov M. B. (1994) Unsaturated hydrocarbons in crude oils. *Org. Geochem.* 21, 189-208.

Frolov E. B., Melikhov V. A. and Smirnov M. B. (1996) Radiolytic nature of n-alkene/n-alkane distributions in Russian Precambrian and Palaeozoic oils. *Org. Geochem.* 24, 1061-1064.

Bücker C. and Rybach L. (1996) A simple method to determine heat production from gamma-ray logs. *Mar. Pet. Geol.* 13, 373-375.

The invention claimed is:

1. A method for dating a residence age (RA), of a petroleum fluid in a petroleum reservoir, comprising:

Determining local matrix nuclear radiation dose rates for a solid reservoir matrix at one or more locations ($dr_Q$), and selecting one or more distinct sample locations within the reservoir each having a distinct matrix radiation dose rate of a matrix radiation;

obtaining reservoir petroleum fluid samples of a reservoir fluid from the one or more distinct sample locations, wherein the reservoir fluid in the samples contains a radiological proxy moiety that is a marker for a proxy chemical transformation of the reservoir fluid in response to a total radiation dose absorbed from the matrix radiation over a geological time span, and where the proxy chemical transformation rate in response to a metered radiation dose of the matrix radiation is determined in a laboratory by irradiation of reservoir fluid samples at dose rates higher than dose rates in the petroleum reservoir;

determining the concentration of the radiological proxy in the reservoir fluid samples from the distinct sample locations, the concentration of the radiological proxy in each sample being proportionate to a total radiation dose for the reservoir fluid sampled at each of the respective sample locations, so that a total radiation dose for each sample ($Q_{total}$) is calculated from the concentration of the radiological proxy in each sample;

assessing a fractional contribution of a local reservoir radiation dose ($Q_{reservoir}$), to the total radiation dose ($Q_{total}$) for each sample; and, calculating the nominal duration of exposure within the reservoir of each of the reservoir fluid samples to the respective local reservoir radiation dose rates ($dr_Q$), to provide the residence age (RA), based on a calculated local radiation dose signal for each sample based on the concentration of the radiological proxy and the local radiation dose rate;

Based on the calculated local radiation dose signal for each sample the concentration of the radiological proxy and the local radiation dose rate.

2. The method of claim 1, further comprising determining the RA of a hydrocarbon reservoir fluid at a plurality of reservoir zones.

3. The method of claim 1, wherein the matrix radiation is gamma radiation, or wherein the metered radiation dose comprises gamma ray photons at dose rates ranging from 0.01 Gy/h to 30 Gy/h.

4. The method of claim 1, wherein the radiological proxy moiety comprises: a measured isotopic or spectroscopic property of a petroleum or petroleum subfraction; or, a concentration of a defined and analytically accessible saturated or aromatic hydrocarbon, or sulphur or oxygen or metal bearing organic compound; or, a bulk concentration of a functional group or structural moiety in the petroleum fluid or in a subfraction thereof; wherein the radiological proxy moiety responds in a defined manner to an incurred dose of the matrix radiation.

5. The method of claim 4, wherein the radiological proxy moiety comprises:
a measured concentration of olefinic carbon or hydrogen; or,
a measured concentration of one or more normal alkanes, acyclic branched chain or cyclic alkanes including biomarker alkanes; or,
a measured concentration of: one or more, alkylated or non-alkylated aromatic hydrocarbons; or, one or more aromatic biomarker compounds; or, an alkylated or non-alkylated aromatic hetero compound containing sulphur, nitrogen, oxygen or another heteroatom.

6. The method of claim 4, wherein a concentration increase of the radiological proxy moiety is used to assess incurred radiation dose; or, wherein a concentration decrease of the radiological proxy moiety is used to assess incurred radiation dose.

7. The method of claim 4, wherein a stable carbon isotopic composition of methane or a light hydrocarbon is used as the radiological proxy moiety.

8. The method of claim 1, wherein a sample specific change in concentration of the radiological proxy moiety is measured in response to an increment of radiation dose, to provide a measured sensitivity to incurred radiation dose ($S_{proxy}$) parameter.

9. The method of claim 1, further comprising determining in an assay a unique quantitative response of the radiological proxy moiety to progressively increasing radiation doses, wherein the radiation doses are comparable to radiation doses experienced by the petroleum fluids in the petroleum reservoir.

10. The method of claim 1, wherein a measured sensitivity of the radiological proxy to incurred radiation dose ($S_{proxy}$), is determined by measuring the chemical and/or stable isotopic composition of an initial reservoir petroleum fluid sample and aliquots of the initial reservoir petroleum fluid after exposure to a laboratory accumulated radiation dose, wherein the laboratory accumulated radiation dose is a dose level within a range of dose levels characteristic of a selection of petroleum reservoirs over geological timescales.

11. The method of claim 1, wherein a reservoir radiation dose ($dr_{total}$) is determined by: measurements with a composite or spectral gamma ray logging tool, or other radiation detection system; or, by applying a radioactive element decay theory based on analysis of radioactive isotope concentrations in the petroleum fluid in the petroleum reservoir, wherein the radioactive isotopes are one or more of uranium, thorium, potassium, radon or other radioactive element isotopes.

12. The method of claim 1, whereby a total radiation dose received by a petroleum fluid sample from the reservoir medium ($Q_{reservoir}$) is determined as a fraction of a total radiation dose ($Q_{total}$) received by the petroleum fluid while in source rock and during migration as determined using the radiological proxy moiety, by comparing the total radiation dose accumulated by a petroleum sample near a more radioactive part of the reservoir with the total radiation dose accumulated by a petroleum sample from a part of the reservoir with low radioactivity and assuming that the total radiation dose ($Q_{total}$) remains essentially constant for all the petroleum fluids in the petroleum reservoir.

13. The method of claim 12, wherein a relative proportions of the total dose rate signal from a gamma-ray log near a more radioactive reservoir location and a gamma-ray log near a less radioactive reservoir section, provides a scaling factor for $Q_{reservoir}$ versus $Q_{total}$.

14. A method for dating residence age of a hydrocarbon reservoir fluid in a hydrocarbon reservoir, comprising:
determining local matrix radiation dose rates for a solid reservoir matrix at a plurality of locations, and selecting a plurality of distinct sample locations within the reservoir each having a distinct matrix radiation dose rate of a matrix radiation;
obtaining a plurality of reservoir fluid samples from two or more of the distinct sample locations, wherein the reservoir fluid in the samples comprises a radiological proxy moiety that is a marker for a proxy chemical transformation of the reservoir fluid in response to a total radiation dose of the matrix radiation over a geological time span, and wherein a proxy chemical transformation rate in response to a metered radiation dose of the matrix radiation is such that a changing concentration of the radiological proxy is measurable over a measurement time span that is less than 1 year, where the metered radiation dose rate is greater than a natural matrix radiation dose rate;
determining the concentration of the radiological proxy in the reservoir fluid samples from distinct sample locations, the concentration of the radiological proxy in each sample being proportionate to a total radiation dose for the reservoir fluid sampled at each of the respective sample locations, so that a total radiation dose signal for each sample ($Q_{total}$) is calculated from the concentration of the radiological proxy in each sample;
calculating a nominal duration of exposure of each of the reservoir fluid samples to the respective matrix radiation dose rates based on the calculated total radiation dose signal for each sample;
setting a concentration of source rock derived radiation dose proxy in the reservoir fluid at a constant value ($Q_{source}$) for at least two of the sample locations, being proximate sample locations within 10 meters of each other in the reservoir, then subtracting $Q_{source}$ from $Q_{total}$ for each sample to obtain a local in-reservoir radiation dose signal ($Q_{reservoir}$) for each sample; and,
assuming the same residence age (RA) for fluids within a reservoir zone containing the proximate sample locations, determining an emplacement time, at which the reservoir fluid samples from the proximate sample locations each became subject to the distinct matrix radiation dose rates at each respective proximate sample location, the difference between present time and the emplacement time being the RA of the hydrocarbon reservoir fluid in the reservoir zone containing the proximate sample locations.

15. The method of claim 14, further comprising determining the RA of the hydrocarbon reservoir fluid at a plurality of reservoir zones, each respectively containing at least two proximate sample locations.

16. The method of claim 14, wherein the matrix radiation is gamma radiation.

17. The method of claim 14, wherein the radiological proxy moiety comprises a measured concentration of olefin hydrogens.

18. The method of claim 14, wherein the metered radiation comprises gamma ray photons with an energy between 0.5 and 2.5 MeV, at dose rates ranging from 0.01 Gy/h to 30 Gy/h.

19. The method of claim 14, further comprising measuring a concentration of the radiological proxy in a source rock for the hydrocarbon reservoir.

20. The method of claim 14, further comprising determining a rate of chemical transformation of the radiological proxy compound in response to the metered radiation dose over a measurement time span that is less than 1 year.

* * * * *